(12) United States Patent
Sharma et al.

(10) Patent No.: US 8,927,537 B2
(45) Date of Patent: Jan. 6, 2015

(54) PATCHES, FORMULATIONS, AND ASSOCIATED METHODS FOR TRANSDERMAL DELIVERY OF ALPRAZOLAM AND OTHER DRUGS

(75) Inventors: Sanjay Sharma, Sandy, UT (US); Kevin S. Warner, West Jordan, UT (US); Jie Zhang, Salt Lake City, UT (US); Guang Yan, West Jordan, UT (US)

(73) Assignee: Nuvo Research Inc., Mississauga, Ontario (CA)

( * ) Notice: Subject to any disclaimer, the term of this patent is extended or adjusted under 35 U.S.C. 154(b) by 159 days.

(21) Appl. No.: 12/340,246

(22) Filed: Dec. 19, 2008

(65) Prior Publication Data

US 2009/0181954 A1 Jul. 16, 2009

Related U.S. Application Data

(60) Provisional application No. 61/009,009, filed on Dec. 21, 2007.

(51) Int. Cl.
| | | |
|---|---|---|
| *A01N 43/62* | (2006.01) | |
| *A61K 31/55* | (2006.01) | |
| *C07D 513/00* | (2006.01) | |
| *C07D 515/00* | (2006.01) | |
| *C07D 487/12* | (2006.01) | |
| *A61K 9/70* | (2006.01) | |
| *A61K 31/485* | (2006.01) | |
| *A61K 31/519* | (2006.01) | |
| *A61K 31/5517* | (2006.01) | |
| *A61K 9/00* | (2006.01) | |
| *A61K 47/10* | (2006.01) | |

(52) U.S. Cl.
CPC ............ *A61K 9/7084* (2013.01); *A61K 31/485* (2013.01); *A61K 31/519* (2013.01); *A61K 31/5517* (2013.01); *A61K 9/0014* (2013.01); *A61K 47/10* (2013.01)
USPC ......................................... 514/220; 540/558

(58) Field of Classification Search
USPC ......................................... 514/220; 540/558
See application file for complete search history.

(56) References Cited

U.S. PATENT DOCUMENTS

| | | | |
|---|---|---|---|
| 4,863,970 | A | 9/1989 | Patel et al. |
| 5,378,473 | A | 1/1995 | Sharma et al. |
| 5,500,222 | A | 3/1996 | Lee et al. |
| 5,580,574 | A | 12/1996 | Behl et al. |
| 6,267,984 | B1 | 7/2001 | Beste et al. |
| 2003/0099694 | A1* | 5/2003 | Cevc et al. ............ 424/449 |
| 2003/0199426 | A1 | 10/2003 | Carrara et al. |
| 2005/0244522 | A1 | 11/2005 | Carrara et al. |
| 2006/0153905 | A1 | 7/2006 | Carrara et al. |
| 2006/0198881 | A1 | 9/2006 | Howard et al. |
| 2006/0280783 | A1 | 12/2006 | Dipietro et al. |
| 2007/0225379 | A1 | 9/2007 | Carrara et al. |

FOREIGN PATENT DOCUMENTS

EP 0491076 6/1992

* cited by examiner

*Primary Examiner* — Sarah Pihonak
(74) *Attorney, Agent, or Firm* — Thorpe North & Western LLP (57) ABSTRACT

The present invention is drawn to transdermal drug formulations, transdermal patches incorporating such formulations, as well as associated methods. The formulations can include about 0.3 wt % to about 5 wt % of a drug, such as alprazolam, about 4 wt % to about 30 wt % water, about 10 wt % to about 40 wt % glycerol, about 0.5 wt % to about 6 wt % oleyl alcohol. Other co-solvents and/or additives can be present to achieve a 100 wt % formulation.

33 Claims, 3 Drawing Sheets

PATCHES, FORMULATIONS, AND ASSOCIATED METHODS FOR TRANSDERMAL DELIVERY OF ALPRAZOLAM AND OTHER DRUGS

BACKGROUND

Oral alprazolam products, such as Xanax®, have been used to treat anxiety disorder and panic disorder. However, oral alprazolam is typically taken once or twice a day, and blood drug concentrations in the patient can swing within a wide range. As such, other formulations and/or delivery methods can provide benefits over traditional delivery approaches.

SUMMARY

The present invention is drawn to transdermal drug formulations, transdermal patches incorporating such formulations, as well as associated methods of use for treating anxiety, panic, or other psychiatric disorders. In one embodiment, a formulation for transdermal delivery of alprazolam or another drug is provided. The formulation can include about 0.3 wt % to about 5 wt % of a drug, e.g. alprazolam, hydromorphone, risperidone, etc., about 4 wt % to about 30 wt % water, about 10 wt % to about 40 wt % glycerol, and about 0.5 wt % to about 6 wt % oleyl alcohol, and optionally about 20 wt % to about 85 wt % propylene glycol. In another embodiment, a formulation for transdermal delivery of a drug can include 0.8 wt % to 1.8 wt % alprazolam, 6 wt % to 15 wt % water, 20 wt % to 35 wt % glycerol, and 2 to 4 wt % oleyl alcohol, and/or optionally about 20 wt % to about 85 wt % propylene glycol. Other more specific concentrations of each of these ingredients can also be used.

The formulations of the present invention can be incorporated into patches for transdermal administration. In one embodiment, a transdermal patch for transdermal delivery of alprazolam can include a transdermal drug formulation as set forth above.

In another embodiment, a patch for transdermal delivery of alprazolam can include a transdermal drug formulation alprazolam, water, glycerol, and oleic acid and have a pH of 7 to 10. The alprazolam can be present in any therapeutically effective concentration, e.g., from about 0.3 wt % to about 5 wt %, or alternatively, from about 1.0 wt % to about 1.5 wt % of the formulation, the water can comprise about 6 wt % to about 15 wt % of the formulation, the glycerol can comprise about 20 wt % to about 35 wt % glycerol of the formulation, and the oleyl alcohol can comprise about 2 wt % to about 4 wt % of the formulation.

In a further embodiment, a method of treating anxiety disorder or panic disorder is provided. The method comprises applying to a transdermal drug formulation to a skin surface of a subject, and maintaining said transdermal drug formulation in contact with said skin surface for a period of at least 48 hours. The transdermal formulation used in the method can include about 0.3 wt % to about 5 wt % alprazolam, about 4 wt % to about 30 wt % water, about 10 wt % to about 40 wt % glycerol, and about 0.5 wt % to about 6 wt % oleyl alcohol. The formulation can be applied as a transdermal patch in one embodiment.

In other embodiments, a transdermal patch for transdermal delivery of hydromorphone can comprise a transdermal drug formulation incorporated in a transdermal patch, wherein the transdermal drug formulation comprises hydromorphone or risperidone, about 6 wt % to about 15 wt % water, about 20 wt % to about 35 wt % glycerol, and from about 2 wt % to about 4 wt % oleyl alcohol, and optionally about 20 wt % to about 85 wt % of an additional solvent.

These and other embodiments will be apparent to one skilled after considering the present disclosure.

DETAILED DESCRIPTION

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a skin irritation reduction agent" includes reference to one or more of such agents.

"Skin" is defined to include human skin, whether intact, diseased, ulcerous, or broken. In one embodiment, the skin is defined to be intact healthy skin.

The term "drug(s)" refers to any bioactive agent that is applied to, into, or through the skin, and which is applied for achieving a therapeutic effect.

The phrase "transdermal delivery" of drug can be targeted to skin tissues just under the skin, regional tissues or organs under the skin, systemic circulation, and/or the central nervous system.

The phrase "permeation enhancing agent" or "permeation enhancer" is defined as a chemical substance that is capable of increasing skin permeability, and sometimes, contributes to skin irritation if used at concentrations sufficient to increase the flux of a drug from being therapeutically insufficient to sufficient.

Unless specified otherwise, "AUC" (area under the plasma drug concentration curve) is defined as the area under the plasma drug concentration curve from zero to 72 hours, with zero hour being the moment the formulation is applied on the skin.

As used herein, a plurality of drugs, compounds, and/or solvents may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Unless otherwise specified, all percentages are in weight. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0 mm" should be interpreted to include not only the explicitly recited values of about 0.01 mm to about 2.0 mm, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. This same principle applies to ranges reciting only one numerical value. Furthermore, such an interpretation should apply regardless of the breadth of the range or the characteristics being described.

It is understood that various drugs can be used in accordance with embodiments of the present invention. Thus, when discussing a drug generically, it is understood to be applicable to many drugs, such as alprazolam, hydromorphone, risperidone, and the like. Alprazolam is of particular interest, and each mention of the term "drug" explicitly includes alprazolam unless the context dictates otherwise.

With these definitions in mind, in accordance with this, a formulation for transdermal delivery of alprazolam can include a drug such as alprazolam, water, glycerol, oleyl alcohol, and optionally propylene glycol. Though not required, generally, the viscosity of the transdermal formulation can be about 20,000 centipoise to about 200,000 centipoise (often with the help of an appropriate thickener).

The drug can be present in the formulation at from about 0.3 wt % to about 5 wt %. In one embodiment, the drug can comprise about 0.5 wt % to about 3 wt % of the formulation. In another embodiment, the drug can comprise from about 0.8 wt % to about 1.8 wt % of the formulation. In yet another embodiment, the drug can comprise from about 1.0 wt % to about 1.5 wt % of the formulation. Alprazolam, hydromorphone, risperidone, and the like, are appropriate candidates for the drug in these embodiments, along with other drugs.

Water can comprise from 4 wt % to about 30 wt % of the total formulation. In one embodiment, water can comprise from 5 wt % to about 25 wt % of the formulation. In another embodiment, water can comprise from 6 wt % to about 15 wt % of the formulation.

The glycerol present in the formulation can comprise from about 10 wt % to 40 wt % about of the formulation. In one embodiment, the glycerol can comprise about 15 wt % to about 37 wt % of the formulation. In another embodiment, the glycerol can comprise about 20 wt % to about 35 wt % of the formulation.

When present in the formulations of the present invention, propylene glycol can comprise from about 20 wt % to about 85 wt %. In one embodiment, the propylene glycol can comprise about 40 wt % to about 70 wt % of the formulation.

The oleyl alcohol present in the formulation can comprise about 0.5 wt % to about 6 wt % of the total formulation. In one embodiment, the oleyl alcohol can comprise about 1 wt % to about 5 wt % of the formulation. In another embodiment, the oleyl alcohol can comprise about 2 wt % to about 4 wt % of the formulation.

For some active drugs, the formulation can comprise about 0.5 wt % to about 6 wt % isostearic acid as a permeation enhancer. In one embodiment, isostearic acid can comprise about 1 wt % to about 5 wt % of the formulation. In another embodiment, isostearic acid can comprise about 2 wt % to about 4 wt % of the formulation.

For some active drugs, the formulation can comprise about 0.5 wt % to about 6 wt % oleic acid as a permeation enhancer. In one embodiment, oleic acid can comprise about 1 wt % to about 5 wt % of the formulation. In another embodiment, oleic acid can comprise about 2 wt % to about 4 wt % of the formulation.

It is also noted that other ingredients can be present in the formulation, such as additional solvents or co-solvents, excipients, fillers, binders and the like, including but not limited to ethylene glycol, propylene glycol, trolamine, butylated hydroxytoluene, edentate disodium, polymers, gelatin, silica, etc. In one embodiment, additional solvent can comprise from about 20 wt % to about 85 wt % of the formulation. In one embodiment, propylene glycol is the additional solvent and comprises about 20 wt % to about 85 wt % of the formulation. In another embodiment, propylene glycol is the additional solvent and comprises from 40 wt % to 70 wt % of the formulation. In another embodiment, propylene glycol is part of the additional solvent and the total additional solvent is from about 20 wt % to about 85 wt %. In another embodiment, the additional solvent may not include propylene glycol, but includes from about 20 wt % to about 85 wt % of additional solvent other than propylene glycol.

In order to provide for enhanced long-term stability of the formulation, in one embodiment, the formulation can include a stabilizing compound such as butylated hydroxytoluene (BHT) or edentate disodium (EDTA). Without being limited by theory, it is believed that the formulation can be stabilized by reducing or eliminating the degradation reaction of drug (e.g., alprazolam) and reducing or eliminating the reaction of the enhancer (oleic acid, oleyl alcohol) in the formulation. As such, any pharmaceutically acceptable compound which can achieve this result can be used (See Example 5, 6, and 8). Stability of the formulation is also enhanced through maintenance of the formulation at a pH of about 7 to about 10 (See Example 5). In one embodiment, the stability of the formulation is such that the degradation rate of the drug, e.g., alprazolam, in the formulation is less than 5% per year at 25° C.

After seeing significant skin irritation caused by some early formulations, without being bound by any particular theory, a skin irritation mechanism and a method to improve the skin irritation while without significantly sacrificing the drug skin permeation flux was discovered (this mechanism was later indicated as valid by experiments described in Examples 2-4). In further detail, conventional wisdom in dermal drug delivery is that formulations containing permeation enhancers, such as oleyl alcohol and oleic acid, cause skin irritation because the enhancers perturb the lipid bilayers, which form the main permeation barrier in the dead skin cells in the stratum corneum as well as the protective walls of live skin cells. Permeation enhancers entering the stratum corneum can lead to delipidation and protein denaturation. Delipidation and protein denaturation lead to enhanced transepidermal water loss and to increased penetration of the enhancers to deeper epidermal layers containing living keratinocytes resulting in skin irritation. However, what has been neglected in this picture is the impact of the non-water solvent(s) in the formulation. A non-water solvent usually has quite different physical-chemical properties than the interstitial fluid in the skin, which is water based. For example, the osmotic pressure of propylene glycol is quite different from that of the interstitial fluid. If a formulation contains no permeation enhancer, the non-water solvent(s)

and the interstitial fluid are separated by the intact stratum corneum, which is an excellent barrier to transdermal permeation. When a suitable permeation enhancer is used, the barrier property of stratum corneum is compromised which increases permeability of formulation components across the skin and allows the substance exchange between the non-water solvent and the interstitial fluid. This exposes the skin cells to the irritating non-water solvent and thus causes skin irritation.

Therefore, without being limited by theory, it is believed that when a certain amount of water is added to the non-water solvent, the differences in the chemical-physical properties between the non-water solvent and the interstitial fluid are reduced, and the irritation potential is thus reduced. Typically, adding water to a non-water-based solvent alters, and often reduces, the permeation driving force which is closely related to the solubility of the drug in the solution. However, the water-concentration vs. solubility curve in such formulations is often such that the solubility decreases slowly until a certain concentration of water is added (referred to hereafter as threshold water concentration). Adding more water beyond this threshold concentration dramatically reduces the solubility and the flux. Therefore, it is believed that there can exist a narrow water concentration range within which the skin irritation potential of the formulation can be significantly reduced but the transdermal drug permeability is not.

The transdermal formulation can also include skin irritation reduction agents other than glycerol and water. It can be beneficial to include additional skin-irritation reduction agent(s) (other than glycerol and water) in the formulation, as the alprazolam or other drug formulation may cause some skin irritation in some patients. In one embodiment, the skin-irritation reduction agent can be a corticosteroid such as hydrocortisone, dexamethasone, or clobetasol. In another embodiment, the skin-irritation reduction agent can be an anti-inflammatory agent such as ketoprofen, diclofenac, or indomethacin. Other skin reduction agents may also be used so long as they do not substantially interfere with or cause degradation of the alprazolam or other primary drug. In certain embodiments, the concentrations and the quantities of the skin-irritation reduction agent in the formulation and the patch are so low that 1) the blood concentration produced by using the patch is far below the toxic level; 2) no appreciable adverse side effect can be caused even if the total quantities of them in the patch are delivered into the body; and/or 3) the concentrations are at or below the active drug concentration threshold for over-the-counter products.

As described above, the transdermal delivery formulations of the present invention can be incorporated into a transdermal patch for administration to a subject. In one embodiment, a transdermal patch for transdermal delivery of alprazolam is provided. The patch can include a transdermal drug formulation having about 0.3 wt % to about 5 wt % alprazolam, about 4 wt % to about 30 wt % water, about 10 wt % to about 40 wt % glycerol, about 0.5 wt % to about 6 wt % oleyl alcohol, and about 20-85 wt % propylene glycol. In another embodiment, the patch can include a transdermal drug formulation having about 0.8 wt % to about 1.8 wt % alprazolam, about 6 wt % to about 15 wt % water, about 20 wt % to about 35 wt % glycerol, from about 2 wt % to about 4 wt % oleyl alcohol, about 20-85 wt % propylene glycol, and which has a pH of 7-10. In each of these embodiments, other co-solvents, fillers, excipients, polymers, irritation reduction agents, etc., can also be present.

When the formulation of the present invention is incorporated into a transdermal patch, the patch can have a formulation-skin contact area of from 2 $cm^2$ to 100 $cm^2$. In one embodiment, each square centimeter of the formulation-skin contact area can generate a mean AUC of at least 20 ng-hr/ml when administered to at least 10 human adults for a 72 hour period of time. In another embodiment, each square centimeter of the formulation-skin contact area can generate a mean AUC of at least 34 ng·hr/ml when administered to at least 10 human adults for a 72 hour period of time. In another embodiment, the total quantity of alprazolam in the patch per $cm^2$ of the transdermal drug formulation-skin contact area can be less than 2 $mg/cm^2$.

When the transdermal formulation is incorporated into a transdermal patch, the patch can be either a reservoir patch or a matrix patch. In one embodiment, the transdermal patch is a matrix patch with an incorporated adhesive, such as a silicone-based adhesive, an acrylic-based adhesive, or a PIB-based adhesive. Alternatively, the patch can be a reservoir patch. Particularly with reservoir patches, the transdermal patch can include a porous membrane, such as in one embodiment, a microporous non-rate-limiting membrane. The transdermal patch can be configured to deliver alprazolam or another primary drug at therapeutically effective rates of at least 0.2 mg/24 hours, and often at least 0.4 mg/24 hours for a period of at least 48 hours. The patches of the present invention can include other patch components or features known in the art include backing layers, release liners, etc.

The formulations of the present invention can be used to treat anxiety and panic disorders. In one embodiment, a method of treating anxiety disorder or panic disorder in a subject is provided. The method includes applying a transdermal drug formulation to a skin surface of a subject and maintaining the transdermal formulation in contact with the skin surface for a period of at least about 48 hours. The transdermal formulation can include about 0.3 wt % to about 5 wt % alprazolam, about 4 wt % to about 30 wt % water, about 10 wt % to about 40 wt % glycerol, and about 0.5 wt % to about 6 wt % oleyl alcohol. Again, as before, other ingredients can also be formulated within the transdermal drug formulation.

The non-active drug part of the formulations in this invention can be used with active drugs other than alprazolam, for achieving the goal of improved skin permeability without unacceptable skin irritation. That is because the advantages of improved permeability without unacceptable skin irritation offered by the formulations of the current invention are expected to work for not only alprazolam but also many other active ingredients. For example, hydromorphone, instead of alprazolam, may be incorporated in the compositions and patch designs of the current invention for transdermal delivery at therapeutically sufficient rates for pain control without unacceptable skin irritation. Risperidone, instead of alprazolam, may be incorporated in the compositions and patch designs of the current invention for transdermal delivery at therapeutically sufficient rates without unacceptable skin irritation for treating schizophrenia or bipolar disorder or other psychiatric disorders.

The following examples illustrate the embodiments of the disclosure that are presently best known. However, it is to be understood that the following are only exemplary or illustrative of the application of the principles of the present disclosure. Numerous modifications and alternative compositions, methods, and systems may be devised by those skilled in the art without departing from the spirit and scope of the present disclosure. The appended claims are intended to cover such modifications and arrangements. Thus, while the present disclosure has been described above with particularity, the following examples provide further detail in connection with what are presently deemed to be the most practical and preferred embodiments of the disclosure.

EXAMPLES

Example 1

Skin Permeation Methodology

Human Epidermal Membrane (HEM) is used as the model membrane for the in vitro flux studies described herein. Dermatome skin is received from various skin banks and is stored in freezer at −20° C. Before starting an experiment, skin is thawed at room temperature until it reaches ambient temperature. Small rectangular pieces of skin membrane are cut and mounted carefully between the donor and receiver chambers of a Franz diffusion cell. The receiver chamber is filled with pH 7.4 phosphate buffered saline (PBS). The experiment is initiated by placing test formulations on the stratum corneum (SC) of the skin sample. Franz cells are placed in a heating block maintained at 37° C. and the HMS temperature is maintained at 35° C. At predetermined time intervals, 5 mL aliquots are withdrawn and replaced with fresh PBS solution. Skin flux ($\mu g/cm^2/h$) is determined from the steady-state slope of a plot of the cumulative amount of drug permeated through the skin versus time.

Example 2

Transdermal Flux using Alprazolam Formulations with and without Irritation Reducing Agents Glycerol may reduce skin irritation potential in certain transdermal drug delivery formulations. It was determined that adding water into certain transdermal drug delivery formulations can reduce skin irritation, and that there may be a narrow range of water concentration in the formulations in order to provide reduced skin irritation without reducing skin drug permeability. Alprazolam formulations containing glycerol and water are prepared to evaluate in vitro permeability. Table 1 lists the ingredients (in weight percentages) of formulations prepared. Formulation 1 is a positive control containing only the permeation enhancer (oleic acid) and alprazolam. Formulation 2 has 30% w/w glycerol added as an irritation reducing excipient and formulations 3 and 4 have glycerol and water. Formulation 3 has 10% water by weight and formulation 4 has 30% water by weight. All formulations have 3% oleic acid and excess alprazolam. Table 2 presents alprazolam permeation flux data across human epidermal membrane from Formulations 1-4. The experimental set up used to generate the data is as described in Example 1.

TABLE 1

Ingredients in the Alprazolam Formulations (% w/w)

| Ingredients* | Formulation 1 | Formulation 2 | Formulation 3 | Formulation 4 |
|---|---|---|---|---|
| Propylene Glycol | 97 | 67 | 57 | 37 |
| Glycerol |  | 30 | 30 | 30 |
| Water |  |  | 10 | 30 |
| Oleic Acid | 3 | 3 | 3 | 3 |

*Excess Alprazolam was used

TABLE 2

| # | Formulation | Skin Flux* ($mcg/cm^2/h$) |
|---|---|---|
| 1 | Propylene Glycol/OA | 33.3 ± 4.5 |
| 2 | Propylene Glycol/OA + 30% Glycerol | 16.8 ± 3.5 |
| 3 | Propylene Glycol/OA + 30% Glycerol + 10% Water | 18.6 ± 2.1 |
| 4 | Propylene Glycol/OA + 30% Glycerol + 30% Water | 5.3 ± 0.6 |

*Skin flux measurements represent the mean and standard deviation of three determinations. Flux measurements reported were determined from the linear region of the cumulative amount versus time plots.

Comparing the in vitro alprazolam skin permeation values of Formulation 2 and Formulation 3, it was observed that addition of 10% water to Formulation 2 did not decrease alprazolam permeation. However, when the amount of water was increased to 30% w/w (Formulation 4), alprazolam permeation decreased from 16.8±3.5 $mcg/cm^2/hr$ to 5.3±0.6 $mcg/cm^2/hr$. The results demonstrate that there is a range of water concentration where flux is not reduced significantly. Increasing the water concentration beyond this range (i.e. close to or greater than 30% w/w) results in a decrease in permeation of alprazolam. The water concentration range in this embodiment is from 2% to 30%, often, the range is from 4% to 20%, and most typically from 6% to 15%.

Example 3

Skin Irritation with and without Irritation Reducing Excipients

The skin irritation potential of Alprazolam Formulations 2 and 3 from the previous example are tested using a standard rabbit skin irritation method. The results are summarized in Table 3 below

TABLE 3

| Formulation | Skin irritation score (higher score indicates more severe irritation) | Desquamation (24 hours after treatment) | Desquamation (72 hours after treatment) |
|---|---|---|---|
| 2 | 2.00 | 6 out of 6 animals | 6 out of 6 animals |
| 3 | 1.67 | 1 out of 6 animals | 1 out of 6 animals |

The above results indicate that the addition of 10% water in the formulation significantly reduces the desquamation in the animals. It should be pointed out that these results are not believed to be drug specific, as alprazolam itself is not known to cause skin irritation. Based on the above experimental data, it is believed that this water concentration range is somewhere from 2% to 30%, from 4% to 20%, and often from 6% to 15%.

Example 4

Skin Irritation Results of Formulation A

Irritation scores from 12 individuals were assessed after removal of a 32 $cm^2$ patch containing Formulation A below. Individuals were assessed over a 24 hour period post removal. Irritation scores for 10 of the 12 volunteers had a score of 2 and the remaining 2 volunteers had a score of 1 immediately after patch removal. A score of 2 refers to volunteers having definite erythema which was readily visible and a score of 1 refers to a dermal response of minimal erythema barely visible. Twenty-four hours post removal the volunteers with an irritation score of 2 were reduced from 10 to 4. By contrast, a placebo formulation containing the components of Formulation A minus the water and glycerol was worn by a 6 volunteers in an in house study. All study participants removed the patches due to excessive irritation after 6-12 hours of wear. This data, combined with the animal study result in the previous example, underscore the value of water and glycerol in reducing the irritation potential of this formulation.

TABLE 4

| Component | Formulation A % w/w |
|---|---|
| API: | |
| Alprazolam, USP[1] | 3.0% |
| Excipients: | |
| Propylene Glycol, USP | 56.4% |
| Glycerin, USP | 27.0% |
| Purified Water, USP | 9.0% |
| Oleic Acid, NF | 3.0% |
| Oleyl Alcohol, NF[1] | — |
| Carbomer Copolymer Type B, NF (Pemulen ® TR1) | 1.5% |
| Trolamine, NF | 0.1% |
| Edetate Disodium, USP | — |
| Butylated Hydroxytoluene, NF | — |
| Formulation pH | 5.8 |

The concentrations of water, glycerol, and oleyl alcohol in a formulation work best when within appropriate ranges. Too low concentrations of water and/or glycerol can cause higher than acceptable skin irritation, while too high concentrations of water and/or glycerol can cause lower than acceptable transdermal flux of the alprazolam. Too high and too low concentrations of oleyl alcohol can cause too much skin irritation or insufficient transdermal alprazolam flux, respectively.

Example 5

Stability Evaluation of Alprazolam Reservoir Formulations

Formulations A-C were prepared with certain ingredients, as outlined below in Table 5. Alprazolam stability was studied in each of the formulations at 25° C. and 40° C. over a 6 month period. The stability results are outlined below in Table 6.

TABLE 5

| Component | Formulation A % w/w | Formulation B % w/w | Formulation C % w/w |
|---|---|---|---|
| API: | | | |
| Alprazolam, USP[1] | 3.0% | 3.0% | 3.0% |
| Excipients: | | | |
| Propylene Glycol, USP | 56.4% | 51.8% | 54.1% |
| Glycerin, USP | 27.0% | 24.1% | 27.0% |
| Purified Water, USP | 9.0% | 9.0% | 9.0% |
| Oleic Acid, NF | 3.0% | 3.0% | — |
| Oleyl Alcohol, NF[1] | — | — | 3.0% |
| Carbomer Copolymer Type B, NF (Pemulen ® TR1) | 1.5% | 2.0% | 1.5% |
| Trolamine, NF | 0.1% | 7.0% | 2.3% |
| Edetate Disodium, USP | — | 0.05% | 0.05% |
| Butylated Hydroxytoluene, NF | — | 0.05% | 0.05% |
| Formulation pH | 5.8 | 7.8 | 7.8 |

TABLE 6

Alprazolam impurity data

| Time | Formulation A % Total Impurities | | Formulation B % Total Impurities | | Formulation C % Total Impurities | |
|---|---|---|---|---|---|---|
| (months) | 25 C. | 40 C. | 25 C. | 40 C. | 25 C. | 40 C. |
| 0 | 0.2 | 0.2 | <0.1 | <0.1 | <0.1 | <0.1 |
| 1 | 0.3 | | <0.1 | <0.1 | <0.1 | <0.1 |
| 3 | 0.4 | 3.2 | | | | |
| 4 | | | <0.1 | 0.16 | <0.1 | <0.1 |
| 6 | 0.8 | 4.5 | <0.1 | 0.26 | <0.1 | <0.1 |

Formulation A samples stored at 25 and 40° C. showed significant growth of alprazolam impurities (chemical reaction products between alprazolam and other ingredient(s) in the formulation) versus Formulation B and C. These results suggest that increasing the pH of the formulation resulted in a substantial decrease in the percent of impurities formed.

Without being limited by theory, it is believed that the formation of impurities at the lower pH at the highest rate was a result of an intramolecular rearrangement of the benzodiazepine ring which is thought to be dependent on pH, temperature, and the formulation excipients. As will be described in the next example, the degradation rate of the enhancer oleic acid in the formulations within the pH range studied is informative, and the formulation produced a very slow and undesirable plasma drug concentration vs. time curve in a human pharmacokinetic study. The enhancer was switched from oleic acid to oleyl alcohol (Formulation C). The undetectable level of impurities of alprazolam formed in this study using oleyl alcohol as the enhancer showed no appreciable impurity growth. This leads to the belief that pH and/or oleic acid are contributors to the degradation of alprazolam.

Example 6

Oleyl Alcohol as Permeation Enhancer

Switching the permeation enhancer from oleic acid (Formulations A, B) to oleyl alcohol was contemplated to further improve the formulation stability. Formulations B and C in Example 5 were placed in 25° C. and 40° C. stability chambers for 6 months for studying their stability. After 6 months at 40° C., oleyl alcohol concentration and the oleic acid concentration were 100% and 95% of the label claim, respectively.

TABLE 7

Enhancer label claim formation.

| Time | Formulation B % Oleic Acid Label Claim | | Formulation C % Oleyl Alcohol Label Claim | |
|---|---|---|---|---|
| (months) | 25° C. | 40° C. | 25° C. | 40° C. |
| 0 | 100 | 100 | 100 | 100 |
| 1 | 100 | 99 | 100 | 100 |
| 4 | 100 | 97 | 100 | 100 |
| 6 | 100 | 95 | 100 | 100 |

The oleyl alcohol concentration of Formulation C was unchanged over the 6 months of this study at 25° C. and 40° C. This data coupled with the corresponding alprazolam degradation rate (Example 5) of Formulation C which has the lowest total alprazolam impurities following 6 months of stability suggests this formulation would be the most stable. In contrast, Formulation B had a relatively significant decrease in the oleic acid concentration after 6 months at 40° C. and slightly higher alprazolam impurities (Example 5). The results of Table 7 suggest that oleyl alcohol based formulation (Formulation C) is a more stable formulation than the oleic acid based formulation (Formulation B).

Example 7

Effectiveness of Oleyl Alcohol as Permeation Enhancer

Formulations B and C were studied in a 12-subject phase I human clinical study. A reservoir patch containing 0.86 gram of either Formulation B or C and having a formulation-skin contact area of 6.23 cm$^2$ was worn on the upper arm of each study subject for 72 hours. Blood samples were taken at predetermined time intervals during the 72 hour wear period plus an additional 72 hours following patch removal. The average alprazolam plasma concentration as a function of time for Formulation B and C are summarized in the FIGS. 1 and 2, respectively The alprazolam plasma concentrations in the 72-hours following the application of Formulation B kept increasing and did not reach steady state during the 72 hour wear period. In contrast, with Formulation C, alprazolam plasma concentrations reached steady state in about 24 hours.

Figure 1:
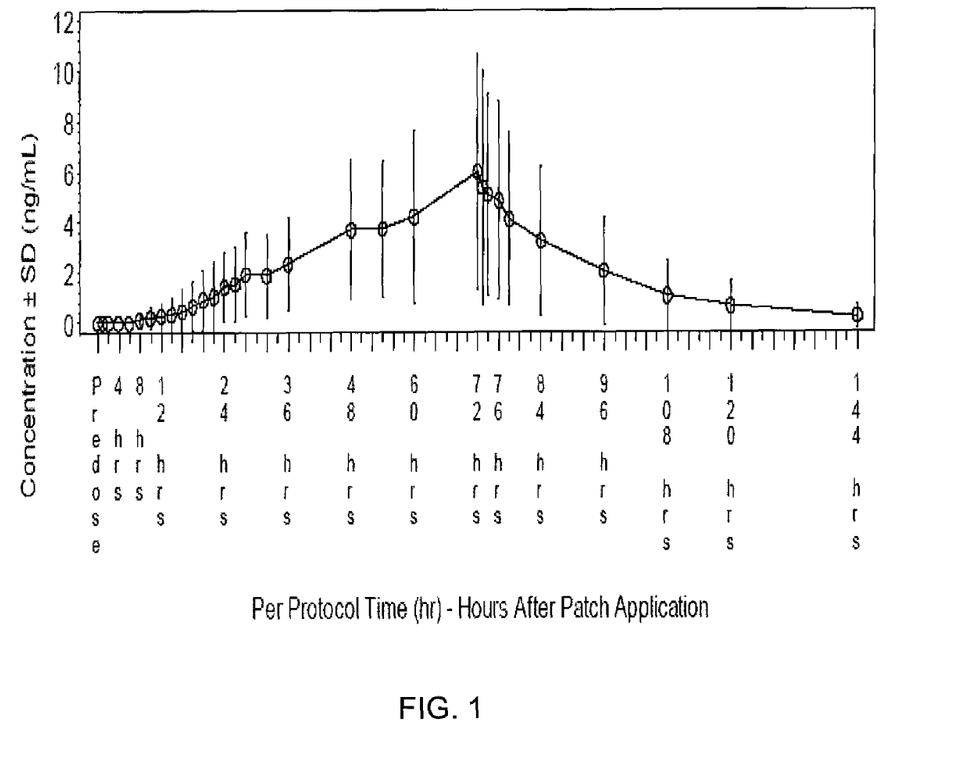
FIG. 1 is a graphical representation of the pharmacokinetic profile of Formulation B in Example 5 (oleic acid formulation with pH adjusted to 7.8). The data was based on a mean of 12 human subjects.
Figure 2:
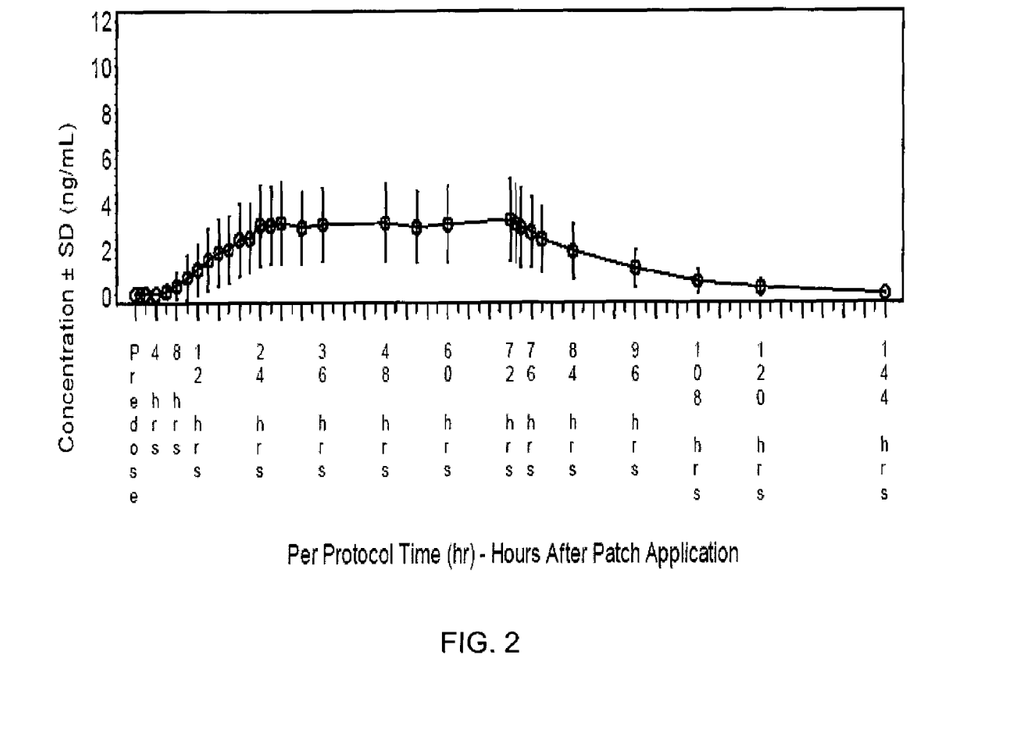
FIG. 2 is a graphical representation of the pharmacokinetic profile of Formulation C in Examples 5 and 10 (oleyl alcohol formulation pH adjusted to 7.8. 3% alprazolam). The data was based on a mean of 12 human subjects.

The alprazolam plasma concentration vs. time profile (pharmacokinetic profile) produced by Formulation C is more desirable even though Formulation B may be able to deliver more drug in the same 72 hours period. That is because consecutive applications of the Formulation C patches (every 72 hours) is expected to produce less peak-trough differences in plasma alprazolam concentrations (due to its ability to reach steady state plasma concentrations sooner), which is believed to be important to the patients.

Example 8

Addition of BHT and EDTA

During the accelerated stability of Formulation A in Example 5, an observation of discoloration of the formulation was noted. Without being limited by theory, it is thought that the discoloration of the formulation was mainly the result of an oxidation reaction of oleic acid in the formulation. In an attempt to reduce or eliminate this discoloration, BHT and EDTA were added to the formulations. Table 1 below summarizes the results of formulations B and C with and without the addition of BHT and EDTA

TABLE 8

Color Change summary

| | | Formulation B | | Formulation C | |
|---|---|---|---|---|---|
| | | With BHT and EDTA | Without BHT and EDTA | With BHT and EDTA | Without BHT and EDTA |
| T0 | T0 | Clear | Clear | Clear | Clear |
| T1 week | RT | Clear | Clear | Clear | Clear |
| | 40° C. | Clear | Clear | Clear | Clear |

TABLE 8-continued

Color Change summary

| | | Formulation B | | Formulation C | |
|---|---|---|---|---|---|
| | | With BHT and EDTA | Without BHT and EDTA | With BHT and EDTA | Without BHT and EDTA |
| T3 week | RT | Clear | Clear | Clear | Clear |
| | 40° C. | Clear | Clear | Clear | Clear |
| T4 week | RT | Clear | Clear | Clear | Clear |
| | 40° C. | Clear | Light yellow | Clear | Clear |
| T8 week | RT | Clear | Clear | Clear | Clear |
| | 40° C. | Yellow | Yellow | Clear | Clear |
| 4 mo/ | RT | Clear | Light Yellow | Clear | Clear |
| 17 wk | 40° C.** | Yellow | Dark Yellow | Clear | Light Yellow |
| 6 mo/ | RT | Clear | Light Yellow | Clear | Clear |
| 26 wk | 40° C.** | Yellow | Dark Yellow | Clear | Light Yellow |

**n = 2;
RT = Room temperature

Coloration of Formulation B without BHT and EDTA was observed after 1 month at 40° C. and after 4 months at room temperature. The color change at 40° C. became more pronounced (turned darker yellow) at each observation following the 1 month evaluation. Addition of BHT and EDTA to Formulation B resolved the discoloration for the room temperature samples up to 6 months and at 40° C. the yellow color was observed after 2 months. Addition of BHT and EDTA to Formulation C showed no discoloration of the samples after 6 months stored at room temperature and 40 C.

Example 9

Alprazolam In Vitro Permeability as a Function of Drug Concentration

Alprazolam formulations with different alprazolam concentrations (but which were otherwise very similar) were prepared (Formulations D and E), as shown in Table 9 below.

TABLE 9

Alprazolam formulation compositions

| Component | Formulation C % w/w | Formulation D % w/w | Formulation E % w/w |
|---|---|---|---|
| API: | | | |
| Alprazolam, USP[1] | 3.0% | 1.0% | 1.5% |
| Excipients: | | | |
| Propylene Glycol, USP | 54.1% | 56.1% | 55.6% |
| Glycerin, USP | 27.0% | 27.0% | 27.0% |
| Purified Water, USP | 9.0% | 9.0% | 9.0% |
| Oleic Acid, NF | — | — | — |
| Oleyl Alcohol, NF[1] | 3.0% | 3.0% | 3.0% |
| Carbomer Copolymer Type B, NF (Pemulen ® TR1) | 1.5% | 1.5% | 1.5% |
| Trolamine, NF | 2.3% | 2.3% | 2.3% |
| Edetate Disodium, USP | 0.05% | 0.05% | 0.05% |
| Butylated Hydroxytoluene, NF | 0.05% | 0.05% | 0.05% |
| Formulation pH | 7.8 | 7.8 | 7.8 |

TABLE 10

| Alprazolam permeation flux | | |
|---|---|---|
| # | Formulation | Skin Flux* (mcg/cm²/h) |
| 1 | C | 4.1 |
| 2 | D | 6.8 |
| 3 | E | 9.2 |

*Skin flux measurements represent the mean of three determinations each from 4 different cadaver skin donors. Flux measurements reported were determined from the linear region of the cumulative amount versus time plots.

It was surprising that Formulations D (1% alprazolam) and E (1.5% alprazolam) produced higher permeation flux than Formulation C (3% alprazolam), as skin flux is usually higher or at least the same with higher drug concentrations.

Example 10

Human Pharmacokinetics of a Formulation Containing 3% Alprazolam

A reservoir patch containing 0.86 gram Formulation C as in Example 9 (3% alprazolam) was tested on 12 human subjects. The reservoir patch had a skin-formulation contact area of 6.23 cm². The patch is applied on the subjects' skin for 72 hours before removal. The mean plasma concentration of alprazolam following the patch applications is shown in FIG. 2. The mean Area Under Plasma Drug Concentration Curve (AUC) values for 0-72 hours, 0-144 hours, and 0-infinity were 172.80, 238.57, and 271.11 ng-hr/mL, respectively. Therefore, each square centimeter of the formulation-skin contact surface area of the patch produced mean AUC of 27.7, 38.3, and 43.5 ng·hr/mL/cm² in the time intervals of 0-72 hour, 0-144 hour, and 0-infinity, respectively.

Example 11

Human Pharmacokinetics of a Formulation Containing 1% Alprazolam

Figure 3:
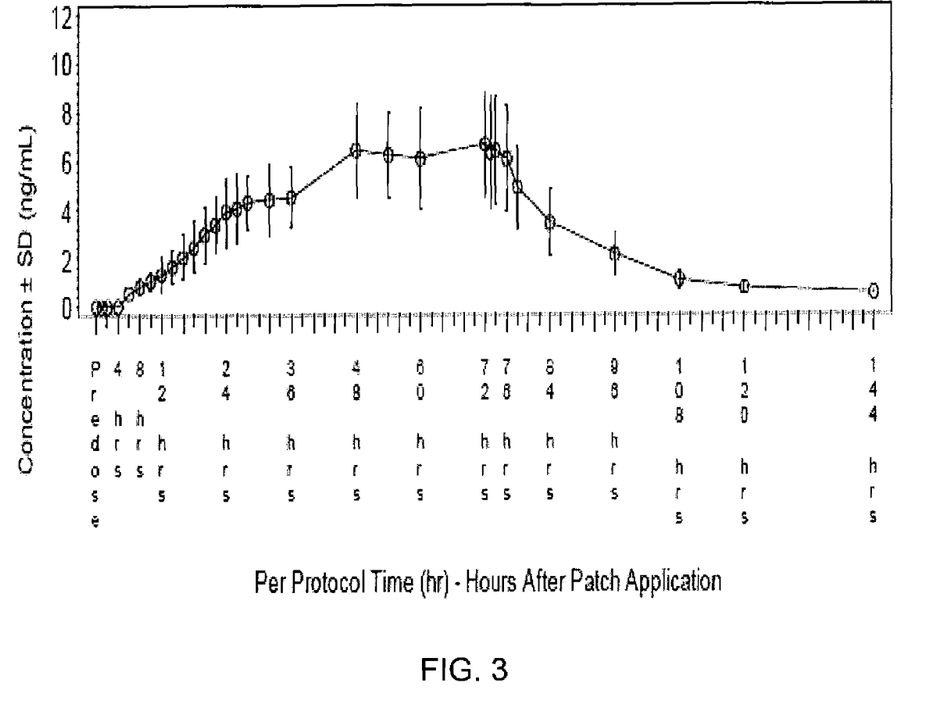
FIG. 3 is a graphical representation of the pharmacokinetic profile of Formulation D in Example 11 (oleyl alcohol formulation pH adjusted to 7.8.1% alprazolam). The data was based on a mean of 12 human subjects.

A reservoir patch containing 0.86 gram Formulation D in Example 9 (1% alprazolam) was tested on 12 human subjects. The reservoir patch had a skin-formulation contact area of 6.23 cm². The patch is applied on the subjects' skin for 72 hours before removal. The mean plasma concentration of alprazolam following the respective patch applications is shown in FIG. 3. The mean Area Under Plasma Drug Concentration Curve (AUC) values for 0-72 hours, 0-144 hours, and 0-infinity were 302.15, 429.21, and 470.22 ng·hr/mL, respectively. Therefore, each square centimeter of the formulation-skin contact surface area of the patch produced mean AUC of 48.5, 68.9, and 75.5 ng·hr/mL/cm² in the time intervals of 0-72 hour, 0-144 hour, and 0-infinity, respectively.

The formulations in Examples 9 and 10 are almost identical, except that the formulation of Example 10 contains 3% alprazolam and the formulation of Example 11 contains 1% alprazolam. Surprisingly, the lower active drug concentration (1%) produced significantly higher (70-80% higher) AUC in human subjects than that by the higher active drug concentration (3%).

The ability of a formulation to deliver alprazolam can be characterized by the area under the plasma drug concentration vs. time curve (AUC) over a certain period of time produced in human subjects by each square centimeter of the formulation-skin contact surface area. For transdermal delivery of alprazolam for treating anxiety disorder or panic disorder, a minimum mean AUC of about 20 ng·hr/ml produced by each square centimeter of formulation-skin contact area over 72 hours is desirable. A mean AUC of about 34 ng·hr/ml produced by each square centimeter of formulation-skin contact area over 72 hours is more typical. The mean AUC as defined here is the mean of AUCs in a randomly selected group of at least 10 healthy adult volunteers.

The higher AUC produced by a unit formulation-skin contact surface area is very beneficial since that allows therapeutic quantities of the active drug to be delivered transdermally with a smaller patch, which is believed to be more patient-friendly and more cost effective. Another benefit of being able to use low concentrations of alprazolam to generate therapeutic levels of blood drug concentrations is minimized abuse potential. Alprazolam is an abusable substance. Minimizing the amount of alprazolam in the new and used patch minimizes the abuse potential. In Formulations C and D above, the total quantities of alprazolam divided by the total formulation-skin contact area are 4.1 and 1.4 mg/cm2, respectively. Formulation D in Example 11 has lower abuse potential.

Example 12

Human Pharmacokinetics of an Alprazolam Formulation

A patch and formulation similar to that used in Example 11 is prepared, except that the patch has a formulation-skin contact area of 20 cm² and contains 2.76 gram of the formulation. The patch produces mean AUC values of 970, 1378, and 1510 ng·hr/mL in 12 human subjects for the 0-72 hours, 0-144 hours, and 0-infinity time periods, respectively Example 13

Human Pharmacokinetics of an Alprazolam Formulation

A patch and formulation similar to that used in Example 11 is prepared, except that the patch has a formulation-skin contact area of 10 cm² and contains 1.38 gram of the formulation. The patch produces mean AUC values of 485, 689, and 755 ng·hr/mL in 12 human subjects for the 0-72 hours, 0-144 hours, and 0-infinity time periods, respectively Example 14

Alprazolam Formulation Including a Corticosteroid

A reservoir patch similar to that in Examples 12 is prepared, except that the formulation further contains 0.2% (by weight) of hydrocortisone for minimizing skin irritation. The total quantity of hydrocortisone in the patch is less than 6 mg. Even if all the hydrocortisone in the patch is absorbed into the patient's body over the 72 hour patch application time, the amount of the hydrocortisone is not expected to cause any appreciable adverse systemic side effect. A hydrocortisone gel containing 0.2% hydrocortisone would also qualify as an over-the-counter product in the USA if it meets other requirements set forth by the US FDA.

Example 15

Alprazolam Formulation Including an Anti-Inflammatory Agent

A patch similar to that in Example 14 is prepared, except that the formulation contains 1% ketoprofen, instead of hydrocortisone, as the skin-irritation reduction agent.

Example 16

Alprazolam Release across Solupor Membrane

A reservoir patch construction (similar to that used in the industry with a backing layer and a skin-contact membrane) was used to hold the formulations similar to the ones in the above examples. A suitable membrane was used to hold the drug formulation in the reservoir of the patch, but not limit the release of drug from the patch. Alprazolam permeation across such a membrane from the formulation was a consideration in the patch development. Continuous EVA (ethylene vinyl acetate) film and a microporous film membrane were evaluated. The EVA film impeded drug release and subsequent permeation across HEM and was therefore not used in the patch construction. A microporous polyethylene membrane (Solupor membrane) with a porosity of 83%, a base weight of 10 g/m², and a Coulter pore size distribution (as measured by bubble point measurements and porosimetry) of 0.05 to 5 microns provided good results. This is a microporous membrane that is not rate limiting to alprazolam permeation from the formulation inside the reservoir patch to the skin (meaning the permeability across the membrane is much faster than that across the skin), while not being permeable to the bulk formulation. In other words, it has the balance of thickness and porosity that allows the alprazolam formulation to easily flow through and does not negatively impact the skin permeation of the formulation, while being able to hold the drug formulation in the reservoir without leakage.

More specifically, alprazolam permeation across HEM was studied in a set up which included placing a Solupor membrane between the HEM and the formulation. The alprazolam permeation across the Solupor and HEM was not statistically different from the permeation of alprazolam when the formulation was placed directly on the HEM, indicating that the membrane does not limit the drug permeation across the skin. In order to best allow for permeation across the membrane, the viscosity of the formulation should not be too high or too low. If the viscosity is too high, the formulation permeability across the Solupor membrane may become low enough to be rate limiting in the entire absorption process. If the viscosity is too low, bulk formulation liquid may ooze out of the reservoir across the Solupor membrane. An acceptable viscosity range can be 7,000 to 700,000 centipoise in certain embodiments, and more often, can range from 20,000 to 200,000 centipoise. Viscosity measurements were performed using a Brookfield Viscometer. Formulations were measured using spindle S-14 at 4 rpm in a small sample adapter at 25° C.

Example 17

Alprazolam In Vitro Permeability as a Function of Drug Concentration

Alprazolam formulations with different alprazolam concentrations (but which were otherwise very similar) were prepared, as shown in Table 11 below.

TABLE 11

Alprazolam formulation compositions

| Component | Formulation F % w/w | Formulation G % w/w | Formulation H % w/w | Formulation I % w/w |
|---|---|---|---|---|
| API: | | | | |
| Alprazolam, USP[1] | 1.2% | 1.3% | 1.4% | 2.0% |
| Excipients: | | | | |
| Propylene Glycol, USP | 55.9% | 55.8% | 55.7% | 55.1% |
| Glycerin, USP | 27.0% | 27.0% | 27.0% | 27.0% |
| Purified Water, USP | 9.0% | 9.0% | 9.0% | 9.0% |
| Oleyl Alcohol, NF[1] | 3.0% | 3.0% | 3.0% | 3.0% |
| Carbomer Copolymer Type B, NF (Pemulen ® TR1) | 1.5% | 1.5% | 1.5% | 1.5% |
| Trolamine, NF | 2.3% | 2.3% | 2.3% | 2.3% |
| Edetate Disodium, USP | 0.05% | 0.05% | 0.05% | 0.05% |
| Butylated Hydroxytoluene, NF | 0.05% | 0.05% | 0.05% | 0.05% |
| Formulation pH | 7.8 | 7.8 | 7.8 | 7.8 |

TABLE 12

Alprazolam permeation flux

| Formulation | Skin Flux (mcg/cm²/h) |
|---|---|
| D* (1% alprazolam) | 9 |
| F* (1.2% alprazolam) | 12 |
| G** (1.3% alprazolam) | 18 |
| H** (1.4% alprazolam) | 18 |
| E** (1.5% alprazolam) | 22 |
| I** (2% alprazolam) | 16 |

*Skin flux measurements represent the mean of three determinations each from 6 different cadaver skin donors. Flux measurements reported were determined from the linear region of the cumulative amount versus time plots.
**Skin flux measurements represent the mean of three determinations each from 3 different cadaver skin donors. Flux measurements reported were determined from the linear region of the cumulative amount versus time plots.

The in vitro alprazolam skin permeation data presented in Table 12 shows that the steady state flux remains relatively unchanged between the alprazolam concentration range of 1.2% to 1.5% and that the flux was higher in this concentration range than the 1% alprazolam formulation.

It is not surprising that the flux value from the present example differs from the alprazolam flux results in Example 9 because of the variability inherent in the experimental set up and the skin samples used. Therefore examples reporting in vitro permeation data should be evaluated independently.

Example 18

Alprazolam In Vitro Permeability as a Function of Drug Concentration

Alprazolam formulations D and E from Example 9 and Formulation G from Example 17 were prepared as shown in the respective examples, each of which contained different alprazolam concentrations, but were otherwise very similar. For convenience the formulations have been restated in Table 13. Table 14 presents alprazolam permeation flux data across human epidermal membrane from Formulations D, E, and G. The experimental set up used to generate the data is as described in Example 1.

TABLE 13

Alprazolam formulation compositions

| Component | Formulation D % w/w | Formulation E % w/w | Formulation G % w/w |
|---|---|---|---|
| API: | | | |
| Alprazolam, USP[1] | 1.0% | 1.5% | 1.3% |
| Excipients: | | | |
| Propylene Glycol, USP | 56.1% | 55.6% | 55.8% |
| Glycerin, USP | 27.0% | 27.0% | 27.0% |
| Purified Water, USP | 9.0% | 9.0% | 9.0% |
| Oleic Acid, NF | — | — | — |
| Oleyl Alcohol, NF[1] | 3.0% | 3.0% | 3.0% |
| Carbomer Copolymer Type B, NF (Pemulen ® TR1) | 1.5% | 1.5% | 1.5% |
| Trolamine, NF | 2.3% | 2.3% | 2.3% |
| Edetate Disodium, USP | 0.05% | 0.05% | 0.05% |
| Butylated Hydroxytoluene, NF | 0.05% | 0.05% | 0.05% |
| Formulation pH | 7.8 | 7.8 | 7.8 |

TABLE 14

Alprazolam permeation flux

| # | Formulation | Skin Flux* (mcg/cm$^2$/h) |
|---|---|---|
| 1 | D | 6 |
| 2 | E | 6.5 |
| 3 | G | 7.5 |

*Skin flux measurements represent the mean of three determinations each from 6 different cadaver skin donors. Flux measurements reported were determined from the linear region of the cumulative amount versus time plots.

The alprazolam flux data generated in this example shows that formulation G generates higher flux than formulations D and E.

It is not surprising that the flux value from the present example differs from the alprazolam flux results in previous examples (i.e., Examples 9 and 17) because of the variability inherent in the experimental set up and the differences in skin samples used. Therefore in vitro permeation values reported in these examples should be evaluated independently. With this in mind, there are some interesting trends can that can be gleaned from this and the previous Examples 9 and 17. Mass transport equations predict that the permeation of a solute (drug) across a rate-limiting membrane is proportional to the drug concentration in the 'donor' or sampling side of the membrane. This concentration dependence holds until the drug is present at its equilibrium solubility, in which case any amount of drug present in the formulation above this solubility value (assuming no supersaturated conditions) will result in no further increase in the drug permeation across the rate-limiting membrane. Examples 9, 17, and 18 show the unexpected result that as the alprazolam concentration approaches the solubility value in the formulation, estimated to be about 1.0 to 1.5 wt % 1.3-1.4% alprazolam, the alprazolam permeation decreases (see Example 9). There was determined to be a region of alprazolam concentrations between 1-1.5% where its permeation was at a maximum. Examples 17 and 18 show that the alprazolam concentration value for maximum skin permeation is around 1.3%. This finding is surprising since as described above, one would predict that when the active drug concentration is increased (foe example from 1.0 to 1.3 to 1.5 to 3.0%), the flux either will increase or stay relatively constant, but will not decrease.

Example 19

Hydromorphone HCl Formulations

Hydromorphone HCl formulations were prepared containing propylene glycol, water, and ISA to evaluate in vitro permeability. Table 15 lists the ingredients (in weight percentages) of the formulations prepared. Table 16 presents alprazolam permeation flux data across human epidermal membrane from Formulations X & Y. The experimental set up used to generate the data is as described in Example 1.

TABLE 15

Ingredients in the Hydromorphone Formulations (% w/w)

| | Formulation | |
|---|---|---|
| Ingredients* | X | Y |
| Propylene Glycol | 87 | 90 |
| Water | 10 | 10 |
| Isostearic Acid** | 3 | |

*Excess hydromorphone was used
**The isostearic acid functions as a permeation enhancer

TABLE 16

| Formulation # | Skin Flux* (mcg/cm$^2$/h) |
|---|---|
| X | 9 |
| Y | 0.2 |

*Skin flux measurements represent the mean of three determinations. Flux measurements reported were determined from the linear region of the cumulative amount versus time plots.

Comparing the skin flux of Formulation X and Formulation Y, it is observed that the presence of isostearic acid in the formulation is important to increasing hydromorphone flux.

Example 20

Transdermal Delivery of Risperidone

A formulation and a patch for transdermal delivery of risperidone for treating schizophrenia or bipolar disorder or other psychiatric disorders are made. The formulation is similar to that in Example 19, except that it does not have alprazolam and contains 3 wt % risperidone.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A formulation for transdermal delivery of a drug, comprising
    from about 0.3 wt % to about 5 wt % of alprazolam,
    from about 4 wt % to about 30 wt % water,
    from about 10 wt % to about 40 wt % glycerol, and
    from about 0.5 wt % to about 6 wt % oleyl alcohol,
    wherein the alprazolam in the formulation has a degradation rate of less than 5% per year at 25° C.

2. A formulation as in claim 1, further comprising from about 20 wt % to about 85 wt % of additional solvent.

3. A formulation as in claim 1, wherein alprazolam comprises about 0.5 wt % to about 3 wt % of the formulation.

4. A formulation as in claim 1, wherein alprazolam comprises about 0.8 wt % to about 1.8 wt % of the formulation.

5. A formulation as in claim 1, wherein alprazolam comprises about 1.0 wt % to about 1.5 wt % of the formulation.

6. A formulation as in claim 1, wherein water comprises about 5 wt % to about 25 wt % of the formulation.

7. A formulation as in claim 1, wherein water comprises about 6 wt % to about 15 wt % of the formulation.

8. A formulation as in claim 1, wherein glycerol comprises about 15 wt % to 37 wt % about of the formulation.

9. A formulation as in claim 1, wherein glycerol comprises about 20 wt % to about 35 wt % of the formulation.

10. A formulation as in claim 1, wherein the oleyl alcohol comprises about 1 wt % to about 5 wt % of the formulation.

11. A formulation as in claim 1, wherein the oleyl alcohol comprises about 2 wt % to about 4 wt % of the formulation.

12. A formulation as in claim 2, wherein the additional solvent includes propylene glycol.

13. A formulation as in claim 1, wherein the formulation has a pH of 7.0 to 10.

14. A formulation as in claim 1, wherein the formulation includes a compound selected from the group consisting of BHT and EDTA.

15. A formulation as in claim 1, wherein the formulation includes a skin irritation reduction agent selected from the group consisting of corticosteroids and anti-inflammatory agents.

16. A formulation as in claim 1, wherein the formulation has a viscosity of about 20,000 to centipoise to about 200,000 centipoise.

17. A formulation as in claim 1, incorporated in a transdermal patch.

18. A transdermal patch for transdermal delivery of alprazolam, comprising:
a transdermal drug formulation incorporated into a transdermal patch, said transdermal drug formulation comprising from about 0.3 wt % to about 5 wt % alprazolam, from about 4 wt % to about 30 wt % water, from about 10 wt % to about 40 wt % glycerol, from about 0.5 wt % to about 6 wt % oleyl alcohol, and optionally from about 20 wt % to about 85 wt % of additional solvent, wherein the alprazolam in the formulation has a degradation rate of less than 5% per year at 25° C.

19. A transdermal patch as in claim 18, wherein the patch has a formulation-skin contact area of from 2 cm² to 100 cm².

20. A transdermal patch as in claim 18, wherein the patch has a formulation-skin contact area of from 5 cm² to 60 cm².

21. A patch as in claim 20, wherein each square centimeter of the formulation-skin contact area generates a mean AUC of at least 20 ng·hr/ml when administered to at least 10 human adults for a 72 hour period of time.

22. A transdermal patch as in claim 20, wherein each square centimeter of the formulation-skin contact area generates a mean AUC of at least 34 ng·hr/ml when administered to at least 10 human adults for a 72 hour period of time.

23. A transdermal patch as in claim 20, wherein each square centimeter of the formulation-skin contact area generates a mean AUC of at least 50 ng·hr/ml when administered to at least 10 human adults for a 72 hour period of time.

24. A transdermal patch as in claim 20, wherein the total quantity of alprazolam in said patch per cm² of the transdermal drug formulation-skin contact area is less than 2 mg/cm².

25. A transdermal patch as in claim 18, wherein the patch includes a microporous non-rate-limiting membrane.

26. A transdermal patch as in claim 18, wherein the patch is configured to deliver alprazolam therapeutically effective rates for a period of at least 48 hours.

27. A formulation for transdermal delivery of alprazolam, comprising:
alprazolam,
about 6 wt % to about 15 wt % water,
about 20 wt % to about 35 wt % glycerol,
about 40% to about 70% propylene glycol, and
about 2 wt % to about 4 wt % oleyl alcohol
wherein the alprazolam in the formulation has a degradation rate of less than 5% per year at 25° C.

28. A formulation as in claim 27 incorporated into a transdermal patch.

29. A formulation as in claim 27, said formulation having a pH of 7-10.

30. A formulation as in claim 27, wherein the alprazolam is present at from about 1.0 wt % to about 1.5 wt %.

31. A transdermal patch for transdermal delivery of alprazolam, comprising:
a transdermal drug formulation incorporated in a transdermal patch, wherein the transdermal drug formulation comprises about 1.0 wt % to about 1.5 wt % alprazolam, about 6 wt % to about 15 wt % water, about 20 wt % to about 35 wt % glycerol, about 40% to about 70% propylene glycol, from about 2 wt % to about 4 wt % oleyl alcohol, and has a pH of 7-10; wherein each square centimeter of the contact area between said formulation and the skin is capable of generating a mean AUC of at least 50 ng.hr/ml when administered to at least 10 human adults for a 72 hour period of time and wherein the alprazolam in the formulation has a degradation rate of less than 5% per year at 25° C.

32. A method of treating anxiety disorder or panic disorder in a subject, comprising:
applying a transdermal drug formulation to a skin surface of a subject, said transdermal formulation comprising from about 0.3 wt % to about 5 wt % alprazolam, from about 4 wt % to about 30 wt % water, from about 10 wt % to about 40 wt % glycerol, and from about 0.5 wt % to about 6 wt % oleyl alcohol and optionally about 20 wt % to about 85 wt % of additional solvent; and
maintaining said transdermal drug formulation in contact with said skin surface for a period of at least 48 hours.

33. A method as in claim 32, wherein the applying step is by applying the transdermal drug formulation to the skin surface by way of a transdermal patch which includes the transdermal drug formulation.

* * * * *